United States Patent [19]

Brown, Jr. et al.

[11] 3,962,461

[45] June 8, 1976

[54] BAIT INSECTICIDE FOR CARPENTER ANTS

[75] Inventors: William L. Brown, Jr., Ithaca, N.Y.; Barbara Brunhuber de Perez, Montreal, Canada

[73] Assignee: Cornell Research Foundation, Inc., Ithaca, N.Y.

[22] Filed: Aug. 28, 1975

[21] Appl. No.: 608,636

Related U.S. Application Data

[63] Continuation of Ser. No. 481,465, June 20, 1974, abandoned.

[52] U.S. Cl. .................................. 424/352; 424/361
[51] Int. Cl.² ................... A01N 9/30; A01N 17/10; A01N 17/14
[58] Field of Search .............................. 424/17, 352

[56] References Cited

UNITED STATES PATENTS 3,220,921  11/1965  Greenbaum ......................... 424/352

OTHER PUBLICATIONS

Journal of Econ. Entomology, vol. 54, No. 6, pp. 1096–1100; vol. 55, No. 3, pp. 405–407; vol. 57, No. 6, pp. 941–945.

Primary Examiner—Donald B. Moyer
Attorney, Agent, or Firm—Theodore C. Wood; Ralph R. Barnard

[57] ABSTRACT

A toxic bait for pest species of insects which feed on sweet, water-based solutions, in which the bait contains suspended recrystallized Mirex in a sweet, aqueous solution.

1 Claim, No Drawings

BAIT INSECTICIDE FOR CARPENTER ANTS

This is a continuation, of application Ser. No. 481,465, filed June 20, 1974 now abandoned.

BACKGROUND OF THE INVENTION

Most forest-dwelling members of the genus Camponotus excavate nests in wood, from which they derive their common name "carpenter ants". Three native species of the northeastern United States differ slightly, but significantly in their nesting habits. Although all prefer to excavate timber in some stage of decay, *Camponotus herculeanus* often makes tunnels in the soil; *C. noveboracensis* nests in very rotten wood and stumps; and *C. pennyslvanicus* nests both in rotten wood and standing trees. It is this latter species that may become a household pest, damaging building timbers and telephone poles. Many different kinds of trees are attacked, although preference is shown for soft woods such as balsam fir, white pine and cedar. This ant species has a wide range, occurring in the eastern United States and southern Canada as far as the hundredth meridian and south to the eastern Gulf States.

Control of these ants has been achieved by spraying the entrance of the nest with insecticides, such as emulsions of DDT or chlordane. Contact dusts, e.g., sodium floride have also been tried, and fair control was achieved with the use of 5% chlordane or 1% dieldrin. The use of wood preservatives such as coal tar creosote has also been employed, but the effectiveness of chemical poisons has proven to be only temporary unless the source of moisture that the ants require in the wood is eliminated. The wood eventually becomes susceptible to new attack. The problem usually lies in the timely detection of the nests before the damage has reached an advanced stage. The usual control is to put chlorinated hydrocarbon powder in likely foraging areas in the hope that the ants will carry it into the nest, but this is not a reliable method. The use of radioactive tracers to locate the nests has been suggested, which method carries with it obvious limitations for general application.

It has also been common practice to exterminate insects such as Camponotus by the use of gaseous poisons or by chopping down the damaged trees, methods hardly useful for controlling the ants in houses.

Some research has been done on the properties of Mirex, (dodecachlorooctahydro-1,3,4-metheno-1H-cyclobuta(cd)pentalene) a slow acting stomach poison, as a suitable toxicant. Echols discusses its use in the control of the Texas leaf-cutting ant *Atta texana* in Journal of Economic Entomology 39:1336–1338. In view of the extensive control program on the imported fire ant *Solenopsis invicta* in the southern States of America, in which Mirex is used, its mode of action is being investigated by the U.S.D.A. Much of this work remains unpublished, although the initial field studies with baits (Bartlett and Lofgren, Journal of Economic Entomology 54:70–73); and evaluations of baits and feeding tests with the fire ant (Lofgren et al., Journal of Economic Entomology 55:405–407 and Stringer et al., Journal of Economic Entomology 57:941–945) have been published.

A bait that contains a poison that kills too rapidly cannot be circulated throughout the whole colony by trophallaxis before the donors are too seriously affected to continue effectively to distribute the poison. The queen may be missed altogether, and the colony will thus survive and soon replenish its numbers. The toxicant also has to act effectively at low concentrations, so that despite dilution through food exchange among large numbers of ants, and despite attenuation through mixing with food collected from other natural sources, the poison will still be effective in eliminating the entire colony.

Mirex ($C_{10}CL_{12}$) is a fully chlorinated closed 10-carbon structure described in the Bulletin of the Entomology Society of America, 1969 15:95. Mirex is a white crystalline solid, odorless, and partially soluble in some organic solvents. Mirex is a slow acting toxicant, which is an important characteristic when used to control such insects as carpenter ants and other insects having a life style such that some members of the colony do not gather food directly but instead receive food from donors that forage.

In the past, Mirex used as an insecticide was formulated in an oil-based solid bait since it is nearly completely insoluble in water. Some insects, e.g., Camponotus, do not feed significantly on oils, and demand food in liquid form in order to be taken up in quantity by the ants.

SUMMARY OF THE INVENTION

In accordance with the principles of this invention, recrystallized Mirex dissolved in Xylene with an emulsifier of Triton X155 (Alkyl aryl polyether alcohol) are sonicated to form a suspension of extremely fine particles which is diluted with honey.

One of the objects of this invention is to provide a slow-acting poison that could be incorporated in an attractive food base which foragers could take back into the nest. They would then have time to distribute it extensively throughout the colony before being themselves too seriously affected.

DESCRIPTION OF THE PREFERRED EMBODIMENT

This invention and other important information is described in the Thesis "Food Distribution within Laboratory Colonies of Carpenter Ants: Camponotus Pennsylvanicus and C. Noveboracensis; and an Investigation into the Problem of "Bait Shyness" in the Control of these Ants Using Mirex Bait" by Barbara Sabine Brunhuber, 1973, made available at Cornell University, Arthur R. Mann Library, Ithaca, New York, on June 21, 1973.

During investigations of effective and practical methods for control of carpenter ants (*Camponotus pennsylvanicus*) it was determined that an attractive bait which is slow acting but lethal is required. It was also discovered that honey had to be a major ingredient in the bait to make it attractive to carpenter ants. Mirex was selected as the toxic ingredient because of its lethal but slow-acting characteristics. Commercial Mirex was recrystallized in order that accurate dosage can be formulated in the bait. Carbon tetrachloride may be used as a solvent for recrystallization (Mirex solubility at room temperature is about 7.2%); however, other solvents may also be used.

Since Mirex cannot be simply mixed with honey to form an attractive bait with accurate dosage and since Mirex is not soluble in water, a solvent such as xylene may be used; however, it has been found that the upper acceptability level of a bait is determined by the amount of xylene that it contains. To minimize the amount of xylene in the bait a supersaturated solution of the ratio of 1 gm. recrystallized Mirex to 9 ml. xylene is prepared, an emulsifier such as Triton X155 is added in the ratio of one drop per ml. of supersaturated solution, and the mixture is then sonicated to break up any large particles and thereby form a suspension. The suspension is then diluted with water in the ratio of 1 part suspension to 10 parts water and the result is a stock suspension of 1% Mirex.

To determine the amount of 1% Mirex stock suspension to be mixed with honey and water to form an attractive bait effective for control of carpenter ants, exhaustive studies and experiments have been conducted and conclusions reached.

Food Distribution

The study of the pathways of food distribution in laboratory colonies was made using the radioisotope $^{32}P$ mixed into honey solutions. In this way the following were investigated:

1. Individual Feeding
   a. The amount of food taken up by single foragers ranged from 4–113% of their body weight. They took longer to fill their crops on the more viscous solutions, and preferred solutions of 50–60% honey-water.
   b. Four to twelve ants could be fed by regurgitation from a single forager before the food chain branched.
   c. There was no significant seasonal effect in amounts taken up by foragers throughout the foraging period.
   d. Rhodamine B dye and $^{32}P$ tracer studies on the passage of food through the ant gut, showed that the crop was emptied in 2–3 days, ending food transfer. Digestion started in the mid gut after 12 hours, and the rectum contained food after 24 hours. Excretion occurred from the fifth day onwards.
   e. There was evidence from starvation tests of the action of a "social stomach" conserving food in groups vs. isolated ants. $^{32}P$ studies showed that digestion took place faster in ants which received food through regurgitation than those which had fed directly from the food source.
   f. Queens were capable of taking up more food than the largest workers.
   g. Large larvae were fed preferentially. They could also pass radioactivity back to the workers. Eggs and pupae did not become radioactive when placed with tracer-labeled workers.
   h. Bait must be in liquid form in order to be taken up in quantity by Camponotus ants.
   i. Carpenter ant workers feed mainly on sweet solutions (in nature, honeydew from plant lice, plant exudations, etc.).
2. Food Distribution in Colonies Tracer studies showed that rapid food exchange took place within the first 24 hours, after which it dropped off quickly. At first the food distribution within the group was uneven; only a few ants received large amounts. A normal distribution was then attained, and later the mode shifted to the smaller amounts. The factors affecting food distribution, i.e., degree of hunger, temperature, group size and polyphenism, were investigated. Evidence of a 'social' as well as a 'hunger' exchange was found. Food was spread more rapidly through large than small groups of workers. There was no clearcut polytheism among the workers of the three sizes, but it appeared that the medias were the most efficient in food uptake and primary regurgitation.

MIREX POISONING

1. The upper acceptability level of the formulation was found to be near 0.1% Mirex; the limiting factor was the xylene used as solvent in bait formulation.
2. Bait containing near 0.005% Mirex was found to be the lowest concentration producing significant mortality in a short time.
3. The question of bait shyness was tested in the laboratory by feeding sublethal dosages of poison and then repoisoning after 15 days with a lethal dose. All the ants took up the poison and died, showing the effects of repoisoning with no evidence of bait shyness at the level of the individual.
4. The lethal times of the toxicant acting on groups of different sizes were tested, and also the effects of temperature and Mirex concentration. The lethal times for queens and major workers were longer than for males and minors. Lowering of temperature and poison concentration both lengthened the lethal times.
5. The amounts of Mirex contained in the various castes at death were analyzed using gas chromatography. If calculated in ppm Mirex, the minor workers contained more toxicant (and died earlier) than the majors. The virgin queens in some instances contained the most Mirex, and survived longest in all cases. The amounts fed to the mature queens by the workers were also determined.
6. The post-pharyngeal glands were found to contain Mirex shortly after poisoning. The function of these glands was investigated in view of the possible trophic use of their secretion. They were found to become radioactive two days after the ants had been fed tracer-labeled food. Some radioactive secretion was shown to be passed to the queen by the workers, but the gland source was not proven.

FIELD CONTROL

Treatment of colonies infesting houses with bait, formulated with honey containing 0.05% of Mirex, showed that the bait was readily taken up by the foragers. No bait shyness was shown with repeated treatment. The foragers of the colonies exhibited the first poison symptoms four days after treatment. Colonies reported over a period from April to mid July were successfully eliminated after twice daily feeding the bait for 1–2 weeks.

According to the provisions of the Patent Statutes, there are described above the invention and specific embodiments thereof. However, it is to be understood that the invention can be practiced otherwise than as specifically described.

What is claimed is:

1. A liquid bait insecticide for ants of the species *Camponotus herculeanus*, *Camponotus noveboracensis* and *Camponotus pennyslvanicus* which comprises the product obtained by sonicating a solution of recrystallized Mirex in xylene, in the presence of an emulsifier, said Mirex being present in a ratio of 1 gm. recrystallized Mirex to 9 ml. xylene, thereby forming a suspension, diluting the suspension with water in the ratio of 1 part suspension to 10 parts water, and mixing said diluted suspension with a honey - water mixture such that the product obtained contains 50–60% of the honey-water mixture, said Mirex being present in the amount of from 0.005 to 0.1% of the total weight of the product.

* * * * *